(12) United States Patent
Liu et al.

(10) Patent No.: US 7,267,009 B2
(45) Date of Patent: Sep. 11, 2007

(54) MULTIPLE-MODE ACOUSTIC WAVE SENSOR

(75) Inventors: James Z T Liu, Belvidere, IL (US); Michael L. Rhodes, Richfield, MN (US); Aziz Rahman, Sharon, MA (US)

(73) Assignee: Honeywell International Inc., Morristown, NJ (US)

( * ) Notice: Subject to any disclaimer, the term of this patent is extended or adjusted under 35 U.S.C. 154(b) by 147 days.

(21) Appl. No.: 11/107,102

(22) Filed: Apr. 14, 2005

(65) Prior Publication Data

US 2006/0230834 A1    Oct. 19, 2006

(51) Int. Cl.
*G01H 11/00* (2006.01)
*G01N 29/00* (2006.01)
(52) U.S. Cl. .................... 73/649; 73/24.06; 73/31.066; 310/313 B; 310/313 D
(58) Field of Classification Search ............... 73/53.01, 73/649
See application file for complete search history.

(56) References Cited

U.S. PATENT DOCUMENTS

| | | | |
|---|---|---|---|
| 4,691,714 A * | 9/1987 | Wong et al. ................ | 600/551 |
| 4,782,332 A | 11/1988 | Cipris et al. ................ | 340/603 |
| 4,792,791 A | 12/1988 | Cipris et al. ................ | 340/603 |
| 5,117,146 A * | 5/1992 | Martin et al. ........... | 310/313 R |
| 5,235,235 A * | 8/1993 | Martin et al. ........... | 310/313 D |
| 5,274,335 A | 12/1993 | Wang et al. ................ | 324/689 |
| 5,301,643 A | 4/1994 | Garcyalny .............. | 123/198 D |
| 5,336,396 A | 8/1994 | Shetley ........................ | 210/90 |
| 5,604,441 A * | 2/1997 | Freese et al. ................ | 324/663 |
| 5,821,425 A | 10/1998 | Mariani et al. | |
| 5,869,763 A | 2/1999 | Vig et al. ...................... | 73/580 |
| 5,878,708 A | 3/1999 | Ruman .................. | 123/196 M |
| 6,044,332 A | 3/2000 | Korsah et al. ................ | 702/76 |
| 6,076,406 A | 6/2000 | Blair et al. .................... | 73/590 |
| 6,260,408 B1 * | 7/2001 | Vig et al. .................. | 73/64.53 |
| 6,293,136 B1 * | 9/2001 | Kim .......................... | 73/19.03 |
| 6,508,100 B2 | 1/2003 | Berndorfer .................... | 73/1.02 |
| 6,557,396 B2 | 5/2003 | Ismail et al. ............... | 73/53.05 |
| 6,776,024 B2 | 8/2004 | Jakoby .......................... | 73/10 |
| 6,786,080 B2 | 9/2004 | Jakoby et al. ............. | 73/54.01 |

(Continued)

OTHER PUBLICATIONS

"SAW Devices as Wireless Passive Sensors", L. Reindl, G. Scholl, T. Ostertag, C. C. W. Ruppel, W. E. Bulst and F. Seifert, Siemens AG Corporate REsearch and Development, Munich, Germany, 1996.*

(Continued)

*Primary Examiner*—Hezron Williams
*Assistant Examiner*—Samir M. Shah
(74) *Attorney, Agent, or Firm*—Kermit D. Lopez; Luis M. Ortiz; William B. Shelby

(57) ABSTRACT

A multiple-mode acoustic wave sensor apparatus includes an acoustic wave device comprising a piezoelectric substrate and at least one electrode on the substrate. When such sensor is used in a wireless configuration, a plurality of antennas can be configured on the substrate in association with the acoustic wave device, wherein each antenna among the plurality of antennas is responsive to varying interrogation signals transmitted wirelessly to the plurality of antennas in order to excite multiple frequency modes via at least one interdigital transducer on the substrate and thereby passively detect multiple and varying parameters of a sensed material utilizing the acoustic wave device.

21 Claims, 5 Drawing Sheets

U.S. PATENT DOCUMENTS

| | | | |
|---|---|---|---|
| 6,799,458 B2 | 10/2004 | Ismail et al. | 73/304 C |
| 6,873,916 B2* | 3/2005 | Kolosov et al. | 702/25 |
| 2004/0035398 A1 | 2/2004 | Klugl et al. | 123/456 |
| 2005/0030332 A1* | 2/2005 | Masuda | 347/19 |
| 2005/0262944 A1* | 12/2005 | Bennett et al. | 73/592 |
| 2006/0230834 A1* | 10/2006 | Liu et al. | 73/649 |

OTHER PUBLICATIONS

"Multi-Frequency and Multi-Mode GHz Surface Acoustic Wave Sensor", W. Seidel and T. Hesjedal, Paul Drude Institute for Solid State Electronics, IEEE Ultrasonics Symposium, 2003.*

Vig, John R., Temperature-Insensitive Dual-Mode Resonant Sensors—A Review, IEEE Sensors Journal, NY, NY, vol. 1, No. 1, Jun. 2001, p. 62-68.

Seidel, W. et al., Multi-Frequency and Multi-Mode CHz Surface Acoustic Wave Sensor, IEEE Ultrasonics Symposium, Honolulu, HI, Oct. 2003, p. 1408-1411.

Grate, J.W., et al. Acoustic Wave Sensors, 1996, p. 37-83.

* cited by examiner

MULTIPLE-MODE ACOUSTIC WAVE SENSOR

TECHNICAL FIELD

Embodiments are generally related to sensing devices and components thereof. Embodiments additionally relate to surface generated acoustic waves, such as shear horizontal surface acoustic wave (SH-SAW), flexural plate wave (FPW), Love mode, acoustic plate mode (APM), shear horizontal acoustic plate mode (SH-APM), and bulk acoustic waves (BAW), including thickness shear mode, torsional mode, overtone modes, and flexural mode components and devices thereof. Embodiments additionally relate to the wireless transmission of detection data.

BACKGROUND OF THE INVENTION

Acoustic wave sensors are utilized in a variety of sensing applications, such as, for example, temperature and/or pressure sensing devices and systems. Acoustic wave devices have been in commercial use for over sixty years. Although the telecommunications industry is the largest user of acoustic wave devices, they are also used for chemical vapor detection. Acoustic wave sensors are so named because they use a mechanical, or acoustic, wave as the sensing mechanism. As the acoustic wave propagates through or on the surface of the material, any changes to the characteristics of the propagation path affect the velocity and/or amplitude of the wave.

Changes in acoustic wave characteristics can be monitored by measuring the frequency or phase characteristics of the sensor and can then be correlated to the corresponding physical quantity or chemical quantity that is being measured. Virtually all acoustic wave devices and sensors utilize a piezoelectric crystal to generate the acoustic wave. Three mechanisms can contribute to acoustic wave sensor response, i.e., mass-loading, visco-elastic and acousto-electric effect. The mass-loading of chemicals alters the frequency, amplitude, and phase and Q value of such sensors. Most acoustic wave chemical detection sensors, for example, rely on the mass sensitivity of the sensor in conjunction with a chemically selective coating that absorbs the vapors of interest resulting in an increased mass loading of the acoustic wave sensor.

Examples of acoustic wave sensors include acoustic wave detection devices, which are utilized to detect the presence of substances, such as chemicals, or environmental conditions such as temperature and pressure. An acoustical or acoustic wave (e.g., SAW/BAW) device acting as a sensor can provide a highly sensitive detection mechanism due to the high sensitivity to surface loading and the low noise, which results from their intrinsic high Q factor. Surface acoustic wave devices are typically fabricated using photolithographic techniques with comb-like interdigital transducers placed on a piezoelectric material. Surface acoustic wave devices may have either a delay line or a resonator configuration. Bulk acoustic wave device are typically fabricated using a vacuum plater, such as those made by CHA, Transat or Saunder. The choice of the electrode materials and the thickness of the electrode are controlled by filament temperature and total heating time. The size and shape of electrodes are defined by proper use of masks.

Surface acoustic wave resonator (SAW-R), surface acoustic wave delay line (SAW-DL), surface transverse wave (STW), bulk acoustic wave (BAW), and acoustic plate mode (APM) all can be utilized in various sensing measurement applications. One of the primary differences between an acoustic wave sensor and a conventional sensor is that an acoustic wave sensor can store energy mechanically. Once such a sensor is supplied with a certain amount of energy (e.g., through RF), the sensor can operate for a time without any active part (e.g., without a power supply or oscillator). This feature makes it possible to implement an acoustic wave in an RF powered passive and wireless sensing application.

Many sensing applications require measurements of multiple parameters. Multiple or groups of sensors are typically employed in these types of applications. Each sensor is dedicated to a particular measurand. In an application such as, for example, oil quality sensing, many factors (e.g., pH, TAN, TBN, viscosity, particulate, lubricity, temperature, flow, pressure, conductivity, humidity, etc.) can contribute to the quality of oil, and thus it is not practical to configure, for example, ten individual sensors in a sensing package. Thus, it would be advantageous to provide a single sensor that can detect multiple parameters. To date, a single sensor for detecting multiple parameters has not been adequately implemented. It is believed that the embodiments disclosed herein overcome the disadvantages of conventional detection systems through the use of a unique surface acoustic sensing arrangement.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensing device.

It is another aspect of the present invention to provide for an improved acoustic wave sensing device It is yet another aspect of the present invention to provide for a wireless and passive multiple mode acoustic wave sensor.

The aforementioned aspects and other objectives and advantages can now be achieved as described herein. A wireless and passive multiple-mode acoustic wave sensor apparatus is disclosed, which includes an acoustic wave device comprising a piezoelectric substrate and at least one interdigital transducer formed as an electrode on the piezoelectric substrate. A plurality of antennas can be configured on the piezoelectric substrate in association with the acoustic wave device, wherein each antenna among the plurality of antennas is responsive to varying interrogation signals transmitted wirelessly to the plurality of antennas in order to excite multiple frequency modes via at least one interdigital transducer on the piezoelectric substrate and thereby passively detect multiple and varying parameters of a sensed material utilizing the acoustic wave device.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
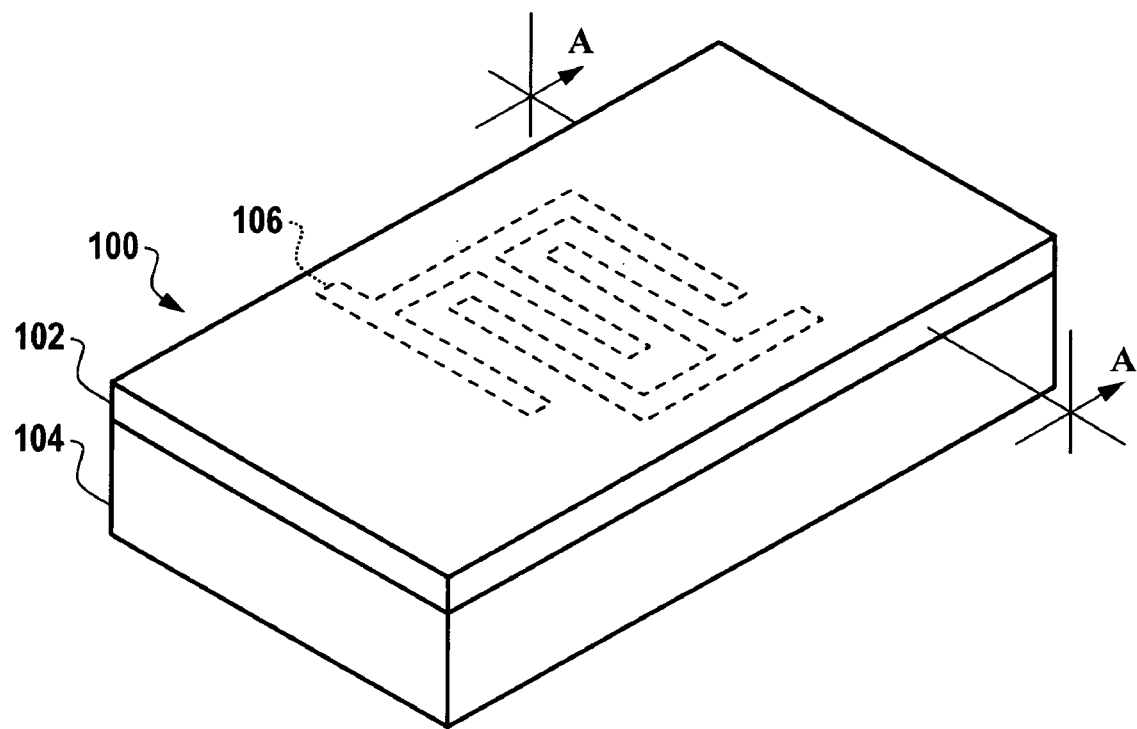
FIG. 1 illustrates a perspective view of an interdigital surface wave device, which can be implemented in accordance with one embodiment.

FIG. 1 illustrates a perspective view of an acoustic wave device 100, which can be implemented in accordance with one embodiment. Acoustic wave device 100 generally includes one or more interdigital transducers (IDT) 106 formed on a piezoelectric substrate 104. The acoustic wave device 100 can be implemented in the context of a sensor chip. Interdigital transducer 106 can be configured in the form of an electrode, depending upon design considerations.

Note that the acoustic wave device 100 represents only one type of acoustic wave device that can be adapted for use with the embodiments disclosed herein. It can be appreciated that a variety of other types (e.g., SH-SAW, BAW, APM, SH-APM, FPW, SH-SAW-DL, SH-SAW-R, etc.) can be utilized in accordance with the embodiments described herein. Additionally, acoustic wave device 100 can be implemented in a variety of shapes and sizes.

Figure 2:
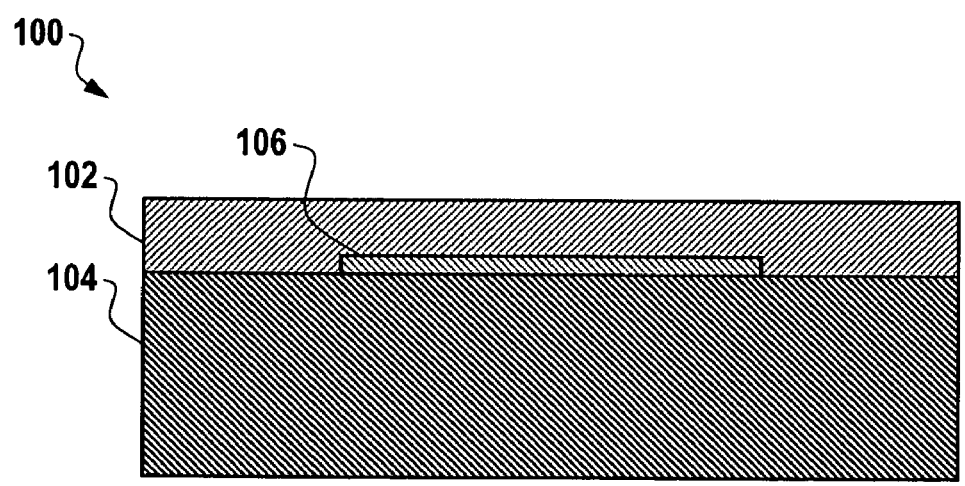
FIG. 2 illustrates a cross-sectional view along line A-A of the interdigital surface wave device depicted in FIG. 1, in accordance with one embodiment.

FIG. 2 illustrates a cross-sectional view along line A-A of the acoustic wave device 100 depicted in FIG. 1, in accordance with one embodiment of the present invention. Piezoelectric substrate 104 can be formed from a variety of substrate materials, such as, for example, quartz, lithium niobate (LiNbO$_3$), lithium tantalite (LiTaO$_3$), Li$_2$B$_4$O$_7$, GaPO$_4$, langasite (La$_3$Ga$_5$SiO$_{14}$), ZnO, and/or epitaxially grown nitrides such as Al, Ga or Ln, to name a few. Interdigital transducer 106 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAl. Third, interdigital transducer 106 can be formed from metal-nonmetal compounds (e.g., ceramic electrodes based on TiN, CoSi$_2$, or WC).

The coating 102 need not cover the entire planar surface of the piezoelectric substrate 104, but can cover only a portion thereof, depending upon design constraints. Coating 102 can function as a guiding layer, which is shown in greater detail herein with respect to FIG. 5. Selective coating 102 can cover interdigital transducer 106 and the entire planar surface of piezoelectric substrate 104. Because acoustic wave device 100 functions as a multiple mode sensing device, excited multiple modes thereof generally occupy the same volume of piezoelectric material. Multiple modes excitation allows separations of temperature change effects from pressure change effects. The multi-mode response can be represented by multiple mode equations, which can be solved to separate the response due to the temperature and pressure.

Figure 3:
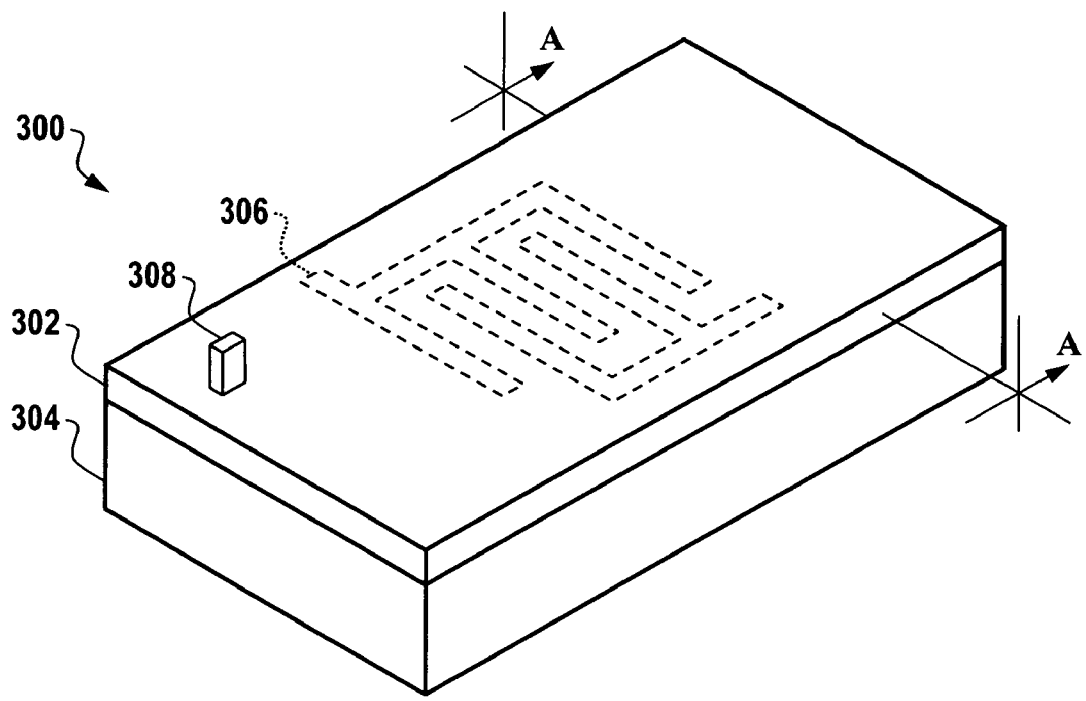
FIG. 3 illustrates a perspective view of an interdigital surface wave device, which can be implemented in accordance with one or more embodiments.
Figure 4:
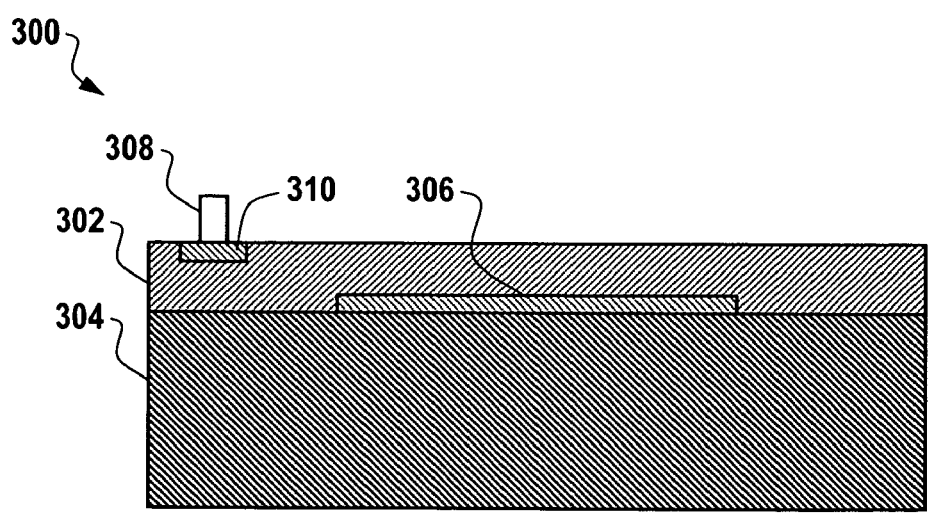
FIG. 4 illustrates a cross-sectional view along line A-A of the interdigital surface wave device depicted in FIG. 3, in accordance with one embodiment.

FIG. 3 illustrates a perspective view of an acoustic wave device 300, which can be implemented in accordance with an embodiment. The configuration depicted in FIGS. 3-4 is similar to that illustrated in FIGS. 1-2, with the addition of an antenna 308, which is connected to and disposed above a wireless excitation component 310 (i.e., shown in FIG. 4). Acoustic wave device 300 generally includes an interdigital transducer 306 formed on a piezoelectric substrate 304.

Acoustic wave device 300 can therefore function as an interdigital surface wave device, and one, in particular, which utilizes surface-skimming bulk wave techniques. Interdigital transducer 306 can be configured in the form of an electrode. A coating 302 can be selected such that a particular species to be measured is absorbed by the coating 302, thereby altering the acoustic properties of the acoustic wave device 300. Various selective coatings can be utilized to implement coating 302.

A change in acoustic properties can be detected and utilized to identify or detect the substance or species absorbed and/or adsorbed by the coating 302. Thus, coating 302 can be excited via wireless means to implement a surface acoustical model. Thus, antenna 308 and wireless excitation component 310 can be utilized to excite multiple modes, thereby allowing separation of temperature change effects from pressure change effects. Such an excitation can produce a variety of other modes of acoustic wave device 300.

FIG. 4 illustrates a cross-sectional view along line A-A of the acoustic wave device 300 depicted in FIG. 3, in accordance with one embodiment of the present invention. Thus, antenna 308 is shown in FIG. 4 disposed above coating 302 and connected to wireless excitation component 310, which can be formed within an area of coating 302. Similar to the configuration of FIG. 2, Piezoelectric substrate 304 can be formed from a variety of substrate materials, such as, for example, quartz, lithium niobate (LiNbO$_3$), lithium tantalite (LiTaO$_3$), Li$_2$B$_4$O$_7$, GaPO$_4$, langasite (La$_3$Ga$_5$SiO$_{14}$), ZnO, and/or epitaxially grown nitrides such as Al, Ga or Ln, to name a few.

Interdigital transducer 306 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAl. Third, interdigital transducer 306 can be formed from metal-nonmetal compounds (e.g., ceramic electrodes based on TiN, CoSi$_2$, or WC). Thus, the electrode formed from interdigital transducer can comprise a material formed from at least one of the following types of material groups: metals, alloys, or metal-nonmetal compounds.

Figure 5:
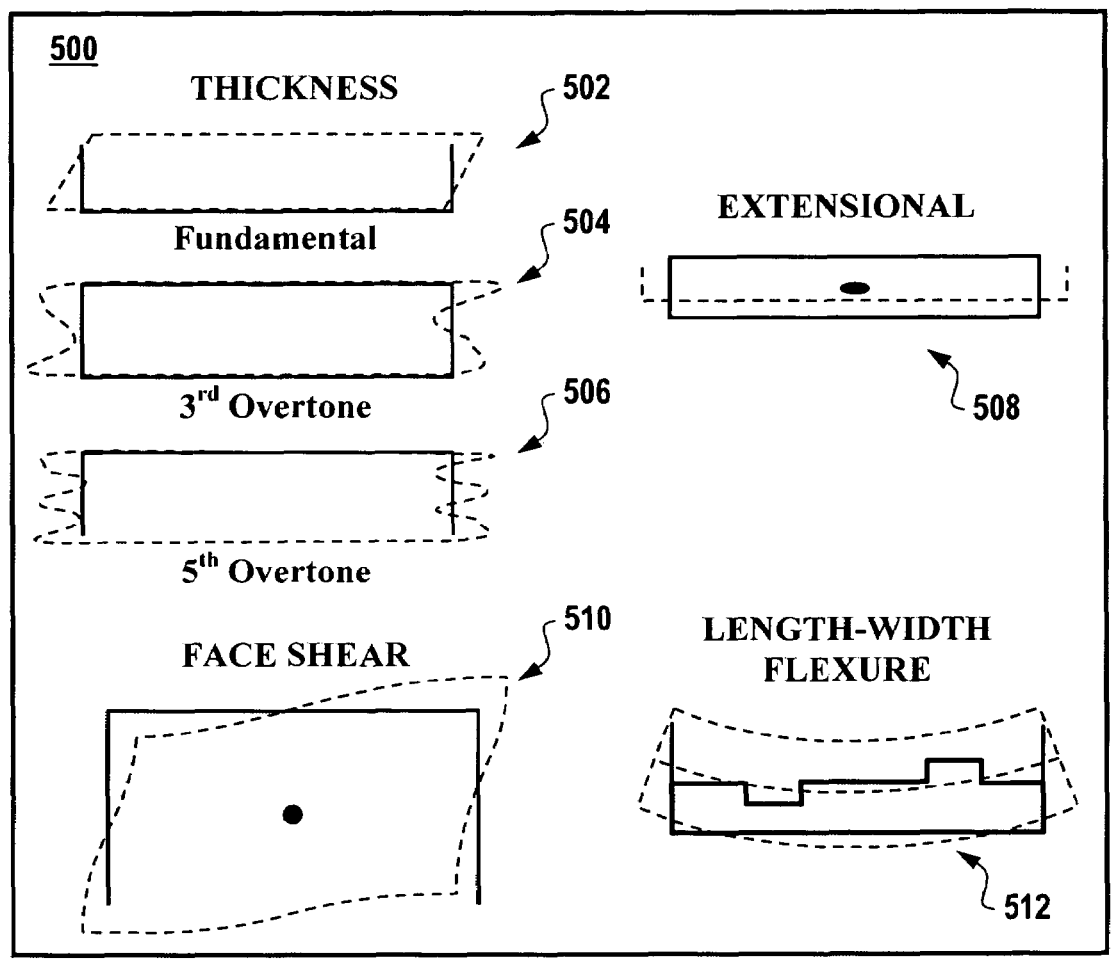
FIG. 5 illustrates multiple modes that can exist in sensor, in accordance with a preferred embodiment.

FIG. 5 illustrates multiple modes 500 that can exist in a wireless sensor as described herein. As indicated in FIG. 5, example modes 500 can include one or more thickness modes, including fundamental 502, 3rd overtone 504, and 5th overtone 506 modes. An extensional mode 508 is also depicted in FIG. 5, along with a face shear mode 510 and a length-width fixture mode 512. It can be appreciated that one or more of such modes can be adapted for use in accordance with one or more embodiments.

Figure 6:
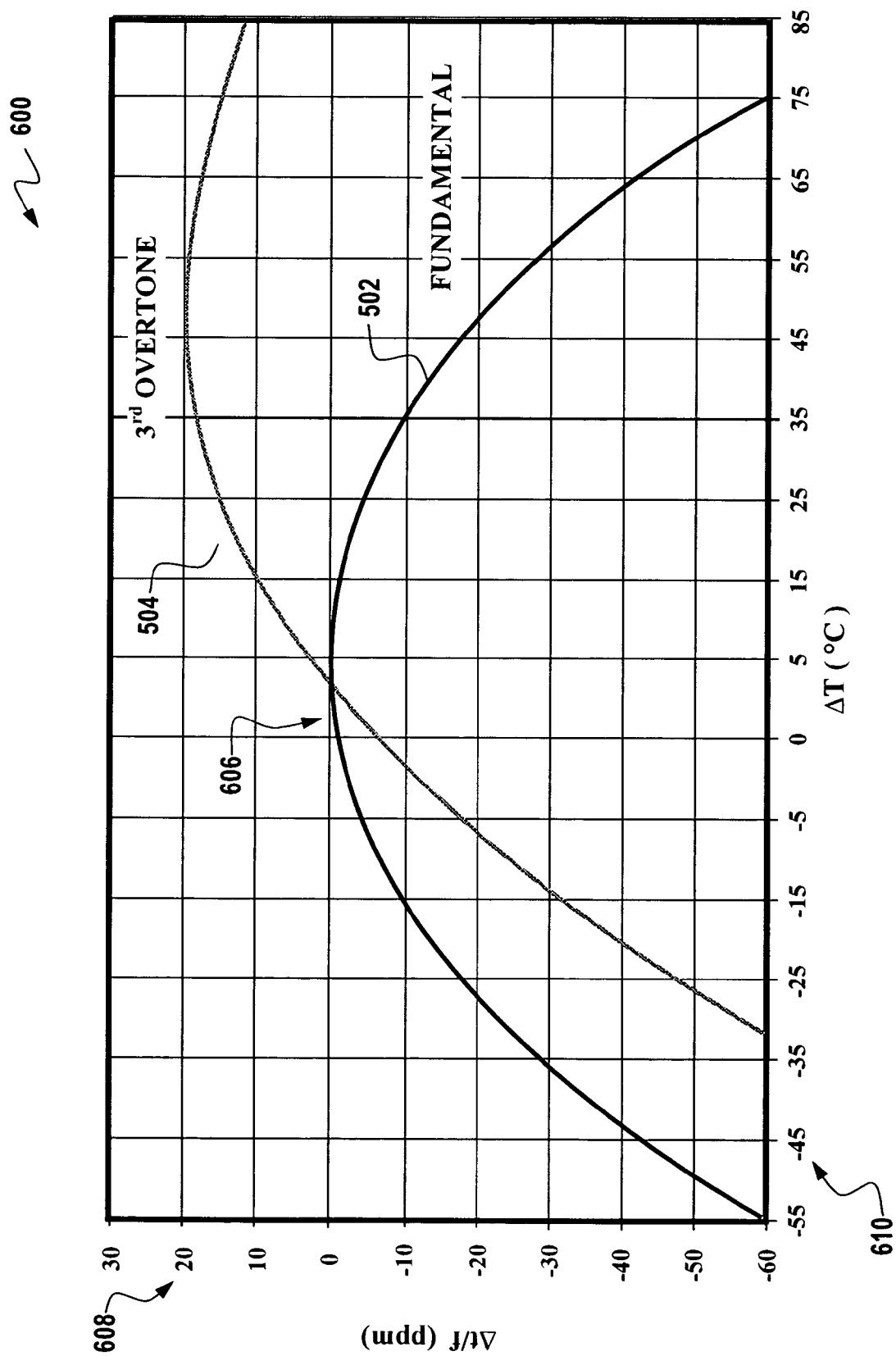
FIG. 6 illustrates a graph depicting fundamental and $3^{rd}$ overtone temperature characteristics of an SC-cut crystal, which can be adapted for temperature compensation applications, in accordance with one embodiment.

FIG. 6 illustrates a graph 600 depicting fundamental and 3rd overtone temperature characteristics of an SC-cut crystal, which can be adapted for temperature compensation applications, in accordance with one embodiment. Note that in FIGS. 5-6, identical or similar parts or elements are generally indicated by identical reference numerals. Thus, graph 600 depicts a curve depicting data representative of 3rd overtone frequency mode 504 and a curve depicting data representative of fundamental frequency mode 502. Note that as utilized herein the terms "frequency mode" and "mode" may be utilized interchangeably to refer to the same phenomena. Graph 600 plots data indicative of a change in frequency over a frequency (y-axis 608) versus a change in temperature (x-axis 610). Graph 600 further illustrates the approximate location 606 representing the Intersection of modes 502 and 504. Based on the data indicated in graph 600, multiple modes can therefore be utilized to accomplish frequency compensation applications.

Figure 7:
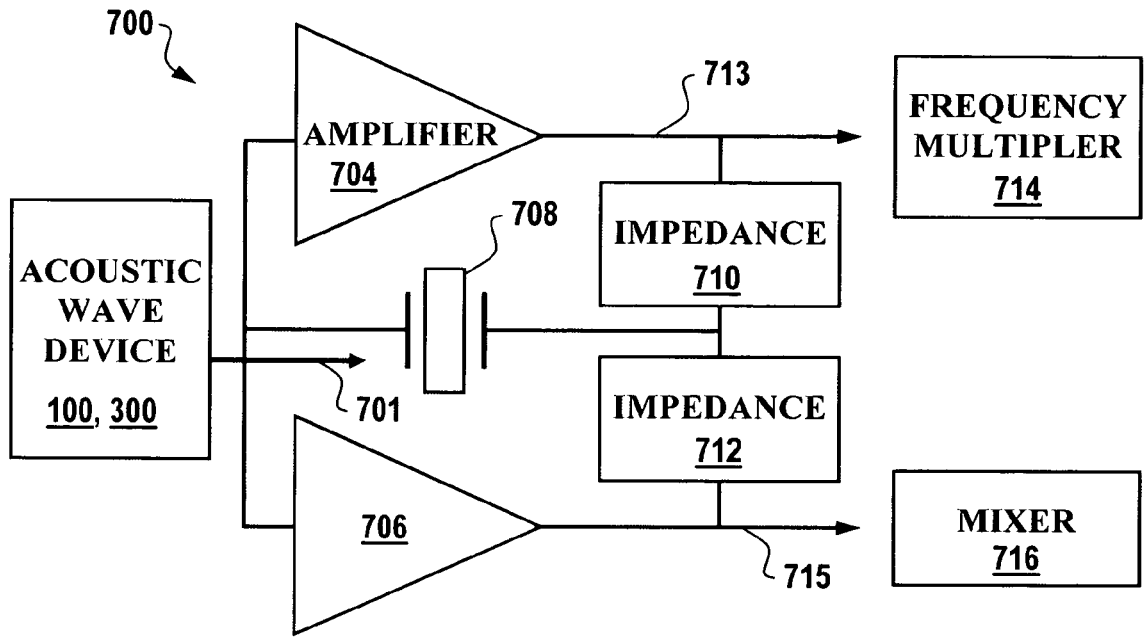
FIG. 7 illustrates a wired dual mode oscillator that can be adapted for use in association with acoustic wave device, in accordance with a preferred embodiment.

FIG. 7 illustrates a wired dual mode oscillator 700 that can be adapted for use in association with acoustic wave device 100 or 300, in accordance with a preferred embodiment. Note that in FIGS. 1-8, identical or similar parts or elements are generally indicated by identical reference numerals. Thus, acoustic wave device 100 or 300 can be utilized in association with the oscillator 700 depicted in FIG. 7. The dual mode oscillator 700 is generally composed of acoustic wave device 100, 300, which can transmit a signal 701 to a transistor 708 having an input connected to an input of an amplifier 704 and an input of an amplifier 706.

The output from amplifier 704 is fed to impedance 710. The output from amplifier 706 is fed to an impedance 712. The output from transistor 708 is connected to both impedance 710 and impedance 712. Output 713 from amplifier 704 and impedance 710 is fed to a frequency multiplier 714, while output 715 from impedance 712 and amplifier 706 is fed to a mixer 716.

Figure 8:
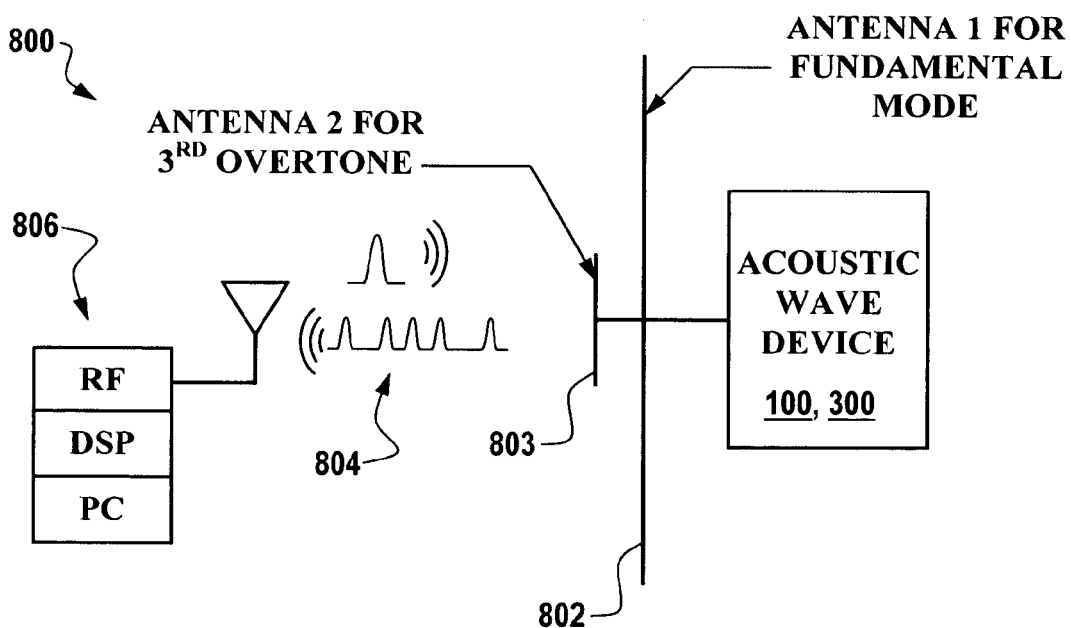
FIG. 8 illustrates a block diagram of a wireless and passive multiple-mode acoustic wave sensing system that can be implemented in accordance with a preferred embodiment.

FIG. 8 illustrates a block diagram of a wireless and passive multiple-mode acoustic wave sensing system 800 that can be implemented in accordance with a preferred embodiment. In general, system 800 incorporates the use of acoustic wave device 100 or 300. A reader unit 806 can transmit excitation signals 804 to a plurality of antennas 802 and 803 associated and connected to acoustic wave device 100, 300. Note that reader unit 806 can be further composed of one or more sub-units, identified in FIG. 8. For example, reader unit 806 can be composed of an RF (Radio Frequency) transmitter/receiver component, a DSP (Digital Signal Processor), and a PC (Personal Computer). Reader unit 806 can be implemented, in some embodiments, as a radar device or radar unit, depending upon design considerations.

Antenna 802, for example, can be utilized to receive signals that excite a fundamental frequency mode 502, while antenna 803 can be utilized to receive signals that excite a $3^{rd}$ overtone frequency mode 504, depending upon design considerations. It is important to note that although FIG. 8 illustrates antennas dedicated to particular frequency modes, such as $3^{rd}$ overtone frequency mode 504 and fundamental frequency mode 502, a variety of other types of frequency modes can be implemented accordingly.

The different excitation modes can be controlled by interrogation electronics (IE) associated with reader unit 806 by providing one or more input signals 804 that possess different frequencies and/or power levels. For example, some excitation modes may possess a higher impedance and may require a higher power level to be excited, hence, the electronics depicted in FIG. 7. In some cases, the acoustic wave sensing device 100, 300 may be optimized or configured so that some predetermined modes can be more easily excited, while suppressing other modes. This may be accomplished in a number of ways, including for example, selecting appropriate design parameters such as electrode thickness, IDT aperture, finger widths and/or spacing of the interdigital transducer(s), the piezoelectric material used, the cut angle of the substrate materials, the orientation of the interdigital transducer(s) relative to the crystalline planes in the piezoelectric material, and so forth.

A variety of acoustic modes may propagate in a piezoelectric half-space, including bulk waves and surface waves. For example, in an interdigital surface (SAW) device design, the substrate materials and crystal orientation can be selected such that that the only surface wave that can be excited is a Rayleigh wave. Other modes of excitation, however, are always present.

Such multiple acoustical modes include, for example, a surface acoustic wave (SAW) mode, shear-horizontal surface acoustic wave (SH-SAW) mode, a pseudo surface acoustic wave (PSAW) mode, and a leak surface acoustic wave (LSAW) mode. Such multiple frequency modes can also include one or more of the following types of modes: flexural plate mode (FPM), acoustic plate shear-horizontal acoustic plate mode (SH-APM), amplitude plate mode (APM), thickness shear mode (TSM), bulk acoustic wave (BAW) mode, transverse mode, surface skimming mode, surface transverse mode, harmonic mode and overtone mode. Note that the multiple frequency modes can be excited through said acoustic wave device to permit a separation of temperature change effects from physical and chemical measurand change effects thereof including pressure, torque, viscosity, density, corrosivity, conductivity, pH, flow, a lubricity, a turbidity, a humidity, a particulate concentration, a total base number, and a total acid number.

In a wireless configuration, such as that of system 800 depicted in FIG. 8, multiple modes can be excited by the interrogation via reader unit 806 in accordance with a preferred embodiment. Multiple modes excitation allows for the separation of temperature change effects from the pressure change effect. Note that in the particular example illustrated in FIG. 8, the $3^{rd}$ overtone is usually about three times the frequency of the fundamental overtone. Thus, the length of antenna 803, for example, may be ⅓, ⅔, 4/3 or 8/3 of the length of the fundamental mode antenna 802, depending upon design considerations.

FIGS. 1-8 generally illustrate a sensor design that utilizes multiple modes of a piezoelectric device. Thus, one sensor is utilized to obtain multiple parameters. Multiple modes excitation allows for the separation of one parameter from another (or others). The multi-mode response can be represented by multiple equations, which can be solved to separate the response due to different measurand. In some cases, interrogation electronics (e.g., see reader unit 806) can be adapted to excite multiple modes in the acoustic wave device 100, 300. This may be accomplished, for example, by transmitting an appropriate input or power signal to the acoustic wave device 100, 300. In some cases, a surface acoustic wave (SAW) mode, shear-horizontal surface acoustic wave (SH-SAW) mode, a pseudo surface acoustic wave (PSAW) mode, and a leak surface acoustic wave (LSAW) mode may be the easiest types of modes to excite, but as indicated herein, other types of modes may also be excited.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A multiple-mode acoustic wave sensor apparatus, comprising:
    a wireless interrogation unit comprising a transmitter and a receiver capable of transmitting varying interrogation signals wherein said varying interrogation signals comprise one or more input signals with varying frequencies and power levels;
    an acoustic wave device comprising a piezoelectric substrate and at least one electrode on said piezoelectric substrate; and
    a plurality of antennas configured on said piezoelectric substrate in association with said acoustic wave device, wherein each antenna among said plurality of antennas is responsive to a different frequency and power level of said varying interrogation signals transmitted wirelessly to said plurality of antennas from said wireless interrogation unit in order to excite multiple frequency modes via at least one interdigital transducer on said piezoelectric substrate and thereby passively detect multiple and varying parameters of a sensed material utilizing said acoustic wave device.

2. The apparatus of claim 1 wherein said varying interrogation signals transmitted wirelessly to said plurality of antennas comprise at least one input signal.

3. The apparatus of claim 1 wherein said varying interrogation signals transmitted wirelessly to said plurality of antennas comprise at least one power signal.

4. The apparatus of claim 1 wherein said multiple frequency modes comprise at least one of the following types of frequency modes: a surface acoustic wave (SAW) mode, shear-horizontal surface acoustic wave (SH-SAW) mode, a pseudo surface acoustic wave (PSAW) mode, and a leak surface acoustic wave (LSAW) mode.

5. The apparatus of claim 4 wherein said multiple frequency modes further comprise at least one of the following types of frequency modes: flexural plate wave (FPW), acoustic plate shear-horizontal acoustic plate mode (SH-APM), amplitude plate mode (APM), thickness shear mode (TSM), bulk acoustic wave (BAW) mode, transverse mode, surface skimming mode, surface transverse mode, harmonic mode and overtone mode.

6. The apparatus of claim 5 wherein said piezoelectric substrate is configured from at least one of the following types of piezoelectric materials: quartz, lithium niobate ($LiNbO_3$), lithium tantalite ($LiTaO_3$), $Li_2B_4O_7$, $AlPO_4$, $GaPO_4$, langasite ($La_3Ga_5Si$)$_{14}$), ZnO, and epitaxially grown nitrides including Al, Ga, or In.

7. The apparatus of claim 6 further comprising a reader unit for wirelessly transmitting said varying interrogation signals to said plurality of antennas in order to excite said multiple frequency modes.

8. The apparatus of claim 1 wherein said acoustic wave device is configured to suppress at least some predetermined frequency modes among said multiple frequency modes while permitting the excitation of other frequency modes thereof via said acoustic wave device.

9. The apparatus of claim 1 wherein an excitation of said multiple frequency modes through said acoustic wave device permits a separation of temperature change effects from pressure change effects thereof.

10. The apparatus of claim 1 wherein said piezoelectric substrate is configured from at least one of the following types of piezoelectric materials: quartz, lithium niobate ($LiNbO_3$), lithium taritalite ($LiTaO_3$), $Li_2B_4O_7$, $AlPO_4$, $GaPO_4$, langasite ($La_3Ga_5Si$)$_{14}$, ZnO, and epitaxially grown nitrides including Al, Ga, or In.

11. The apparatus of claim 1 wherein said electrode comprises a material formed from at least one of the following types of material groups: metals, alloys, or metal-nonmetal compounds.

12. The apparatus of claim 1 further comprising a reader unit for wirelessly transmitting said varying interrogation signals to said plurality of antennas in order to excite said multiple frequency modes.

13. The apparatus of claim 1 wherein said excitation of said multiple frequency modes through said acoustic wave device permits a separation of temperature change effects from physical and chemical measurand change effects thereof including pressure, torque, viscosity, density, corrosivity, conductivity, pH, flow, a lubricity, a turbidity, a humidity, a particulate concentration, a total base number, and a total acid number.

14. A multiple-mode acoustic wave sensor method, comprising the steps of:
    providing a wireless interrogation unit comprising a transmitter and a receiver capable of transmitting varying interrogation signals wherein said varying interrogation signals comprise one or more input signals with varying frequencies and power levels;
    forming an acoustic wave device comprising a piezoelectric substrate and at least one interdigital transducer formed as an electrode on said piezoelectric substrate; and
    configuring a plurality of antennas on said piezoelectric substrate in association with said acoustic wave device, wherein each antenna among said plurality of antennas is responsive to a different frequency and power level of said varying interrogation signals transmitted wirelessly to said plurality of antennas from said wireless interrogation unit in order to excite multiple frequency modes via at least one interdigital transducer on said piezoelectric substrate and thereby passively detect multiple and varying parameters of a sensed material utilizing said acoustic wave device.

15. The method of claim 14 further comprising the step of exciting said multiple frequency modes through said acoustic wave device in order to separate temperature change effects from pressure change effects thereof.

16. The method of claim 14 further comprising the step of exciting said multiple frequency modes through said acoustic wave device to separate temperature change effects from torque change effects thereof.

17. The method of claim 14 further comprising the step of exciting said multiple frequency modes through said acoustic wave device to separate temperature change effects from viscosity change effects thereof.

18. The method of claim 14 further comprising the step of exciting said multiple frequency modes through said acoustic wave device to separate temperature change effects from density change effects thereof.

19. The method of claim 14 further comprising the step of exciting said multiple frequency modes through said acoustic wave device to separate temperature change effects from corrosivity change effects thereof.

20. The method of claim 14 further comprising the step of exciting said multiple frequency modes through said acoustic wave device to permit a separation of temperature change effects from physical and chemical measurand change effects thereof including conductivity, pH, flow, a lubricity, a turbidity, a humidity, a particulate concentration, a total base number, and a total acid number.

21. The method of claim 14 further comprising a reader unit for wirelessly transmitting said varying interrogation signals to said plurality of antennas in order to excite said multiple frequency modes.

* * * * *